(12) United States Patent
Shiue

(10) Patent No.: US 7,966,701 B2
(45) Date of Patent: Jun. 28, 2011

(54) ADJUSTABLE RATCHET BUCKLE

(75) Inventor: Chih-Cheng Shiue, Taipei (TW)

(73) Assignee: Qbas Co., Ltd., Taipei (TW)

( * ) Notice: Subject to any disclaimer, the term of this patent is extended or adjusted under 35 U.S.C. 154(b) by 624 days.

(21) Appl. No.: 12/133,891

(22) Filed: Jun. 5, 2008

(65) Prior Publication Data

US 2009/0300888 A1  Dec. 10, 2009

(51) Int. Cl.
- A62B 9/04 (2006.01)
- B63C 11/02 (2006.01)
- A41F 1/00 (2006.01)
- A61F 9/02 (2006.01)
- G02C 1/00 (2006.01)

(52) U.S. Cl. ........ 24/170; 24/68 E; 24/193; 24/265 BC; 2/452; 351/43

(58) Field of Classification Search .......... None
See application file for complete search history.

(56) References Cited

U.S. PATENT DOCUMENTS

| | | | | |
|---|---|---|---|---|
| 215,956 A * | 5/1879 | Miller | | 24/574.1 |
| 4,607,398 A * | 8/1986 | Faulconer | | 2/452 |
| 4,727,630 A * | 3/1988 | Alan | | 24/593.11 |
| 5,611,644 A * | 3/1997 | Lutz | | 405/186 |
| 6,185,794 B1 * | 2/2001 | Maggi | | 24/170 |
| 6,350,030 B2 * | 2/2002 | Fujima | | 351/43 |
| 6,691,377 B2 * | 2/2004 | Pan | | 24/170 |
| 6,766,540 B2 * | 7/2004 | Kawashima | | 2/452 |
| 6,832,394 B1 * | 12/2004 | Chiang | | 2/428 |
| 6,859,947 B2 * | 3/2005 | Lee | | 2/428 |
| 6,871,386 B2 * | 3/2005 | Chen-Lieh | | 24/168 |
| 6,966,102 B2 * | 11/2005 | Shiue | | 24/196 |
| 7,134,149 B2 * | 11/2006 | Sato | | 2/431 |
| 7,162,778 B2 * | 1/2007 | Pan | | 24/170 |
| 7,275,536 B2 * | 10/2007 | Godoy | | 128/207.11 |
| 7,458,134 B2 * | 12/2008 | Shiue | | 24/68 E |
| 7,571,520 B2 * | 8/2009 | Shiue | | 24/265 BC |
| 7,640,633 B2 * | 1/2010 | Chou | | 24/68 E |
| 7,665,190 B2 * | 2/2010 | Weng | | 24/170 |
| 7,810,175 B2 * | 10/2010 | Chiang | | 2/448 |
| 7,836,561 B2 * | 11/2010 | Vaccaro et al. | | 24/68 E |
| 2006/0032027 A1 * | 2/2006 | Shiue | | 24/191 |
| 2007/0256283 A1 * | 11/2007 | Chiang | | 24/193 |
| 2008/0244875 A1 * | 10/2008 | Chou | | 24/170 |
| 2008/0289160 A1 * | 11/2008 | Chou | | 24/68 R |
| 2009/0100645 A1 * | 4/2009 | Weng | | 24/170 |
| 2009/0205114 A1 * | 8/2009 | Chiang | | 2/428 |
| 2009/0229086 A1 * | 9/2009 | Chiang | | 24/170 |

* cited by examiner

*Primary Examiner* — Jack W. Lavinder
(74) *Attorney, Agent, or Firm* — Guice Patents PLLC

(57) ABSTRACT

A buckle includes a strap slidably looped around a strut proximate a front opening of a housing, a spring-biased, lever-like ratchet having front and rear sections and a front engagement tooth adapted to matingly engage with one of a plurality of rack teeth on an upper surface of the strap, and two opposite pivotal arms extending outside of the housing. Pressing the arms will push down the rear section to lift the front section to disengage the engagement tooth from the rack tooth, thereby adjusting the buckle in discrete increments to tighten the strap.

4 Claims, 3 Drawing Sheets

US 7,966,701 B2

ADJUSTABLE RATCHET BUCKLE

BACKGROUND OF THE INVENTION

1. A Field of Invention

The invention relates to ratchet buckles and more particularly to such a ratchet buckle having a strap slidably looped around a strut proximate a front opening of a housing, a spring-biased, lever-like ratchet adapted to engage with one transverse tooth of a rack of teeth on an upper surface of the strap, and two opposite arms such that pressing the arms will adjust the buckle in discrete increments to tighten the strap.

2. Description of Related Art

Ratchet buckles are widely used for securing together two objects by cooperating with a strap. One advantageous benefit of the ratchet buckle is its tension adjustability Therefore, ratchet buckles can be found in many applications including masks, swim goggles, etc.

One type of conventional ratchet buckle includes a housing having two opposite pivotal arms extending outside thereof the arm having a latched end, and a strap having a rack of teeth on its upper surface. An individual may press and pivot the arms to unfasten the strap prior to adjusting the tension of the strap. However the well known adjustable ratchet buckle is not precise in tension adjustment. Further, components are subject to damage after a short period of time of operation. Thus, it is desirable to provide a novel adjustable ratchet buckle in order to overcome the inadequacies of the prior art.

SUMMARY OF THE INVENTION

It is therefore one object of the invention to provide an adjustable ratchet buckle comprising a strap slidably looped around a strut proximate a front opening of a housing, a spring-biased, lever-like ratchet having front and rear sections and a front engagement tooth adapted to lockingly engage with one tooth of a rack of teeth on an upper surface of the strap, and two opposite arms such that pressing the arms will lift the front section to disengage the engagement tooth from the rack tooth, thereby adjusting the buckle in discrete increments to tighten the strap.

It is another object of the invention to provide an adjustable ratchet buckle having two opposite arms exposed at both sides of a housing, and a ratchet within the housing. Both the arms and the ratchet are durable and can be manipulated precisely, thereby effecting a precise tension adjustment of strap.

The above and other objects, features and advantages of the invention will become apparent from the following detailed description taken with the accompanying drawings.

DETAILED DESCRIPTION OF THE INVENTION

Figure 1:
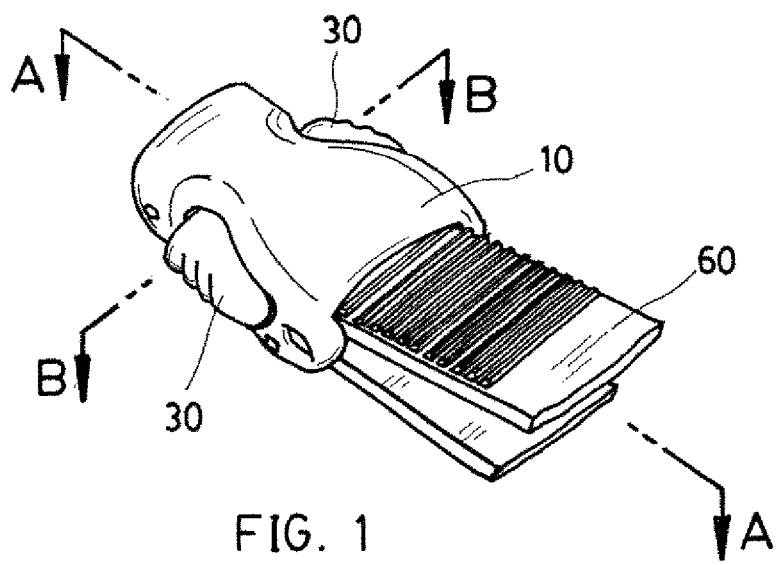
FIG. 1 is a perspective view of a preferred embodiment of adjustable ratchet buckle according to the invention.
Figure 2:
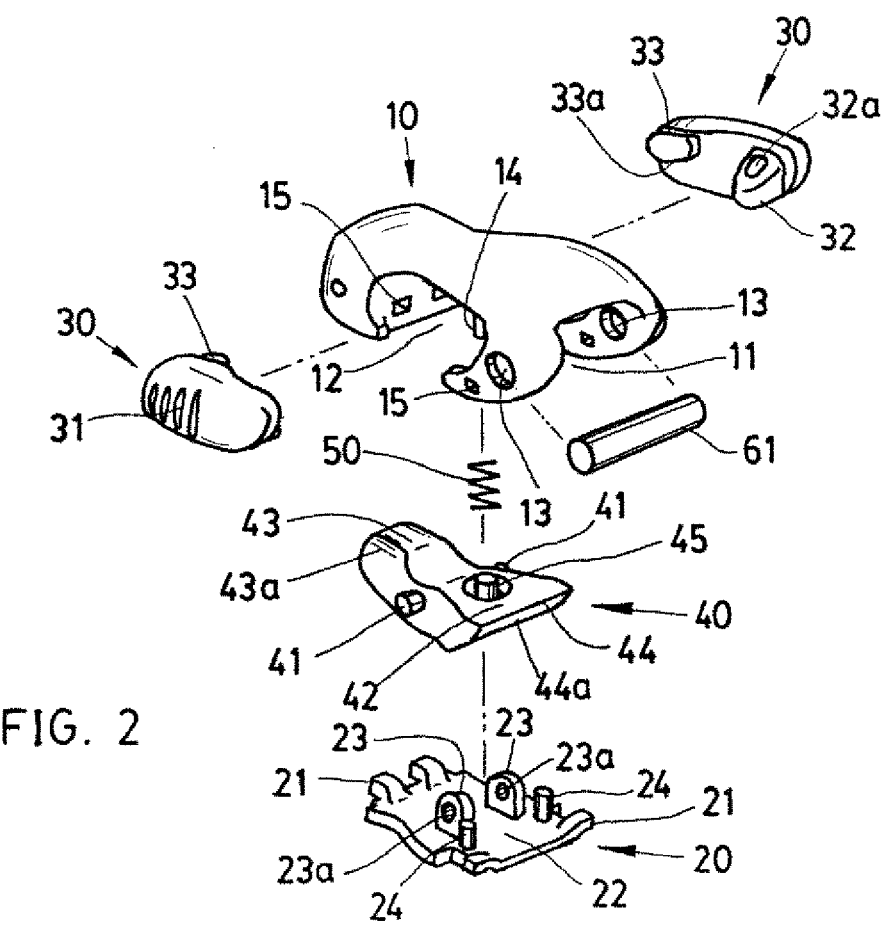
FIG. 2 is an exploded view of the ratchet buckle.

Referring to FIGS. 1 and 2, an adjustable ratchet buckle in accordance with a preferred embodiment of the invention comprises a cover 10, a base 20, two arms 30, a ratchet 40, a spring 50, and a strap 60. Each component is discussed in detail below.

A housing is composed of the cover 10 and the base 20. The ratchet 40 is provided in the housing. A front opening 11 is formed in the cover 10 for permitting the strap 60 to insert thereinto. Two openings 12 are formed on opposite sides of the cover 10 for permitting the arms 30 to dispose therein. The rear end of the cover 10 is secured to an object such as mask, goggles, etc.

The cover 10 is somewhat curve in shape. Two holes 13 are provided on both sides of the front opening 11. A strut 61 is secured between the holes 13. A first stub 14 is formed on the bottom of the top surface of the cover 10. A plurality of through apertures 15 are formed in the cover 10.

The base 20 comprises a plate member 22, two opposite ears 23 proximate both sides of the plate member 22, the ear 23 having a through hole 23a, two pins 24 besides the ears 23 for pivotably mounting the arms 30 thereon, and a plurality of front and rear projections 21.

The arm 30 comprises a toothed trigger 31 on an outer surface, a rear protrusion 33 on an inner surface, the protrusion 33 having an inclined bottom plane 33a, and a front protuberance 32 on the inner surface, the protuberance 32 having a longitudinal hole 32a rotatably put on the pin 24. Hence, the arms 30 are adapted to pivot about the pins 24. The rear end of the trigger 31 will be stopped by the rear end of the side opening 12 when the arms 30 pivot outwardly (i.e., releasing the arms 30). Hence, the arms 30 are allowed to pivot in a limited angle as detailed later The ratchet 40 is somewhat curve at both ends. The ratchet 40 is provided in the housing consisting of the cover 10 and the base 20. The ratchet 40 comprises two pins 41 in the midpoints of both sides, the pins 41 being rotatably inserted into the through holes 23a (i.e., the pins 41 being served as fulcrum), a front section 42, an engagement tooth 44 on the front end of the front section 42, the engagement tooth 44 having an inclined plane (or a curved plane in other embodiments) 44a, a rear section 43 having two rounded top corners (or inclined planes in other embodiments) 43a on both sides, and a second stub 45 on the top of the engagement tooth 42 aligned with the first stub 14. The spring 50 has both ends put on the stubs 14, 45. That is, the spring 50 is biased between the ratchet 40 and the bottom of the top of the cover 10.

After mounting the ratchet 40 in the cover 10 by assembling with the base 20, and mounting the arms 30 on the pins 24, the projections 21 are matingly inserted into the through apertures 15 for assemble the cover 10 and the base 20 as a complete housing. Note that the fastening of the cover 10 and the base 20 may be implemented in a fashion different from the one described above. Hence, a lever-like ratchet 40 is mounted. Note that the engagement tooth 44 may be replaced by a detent member having the same function as the engagement tooth 44 as detailed later.

Figure 3:
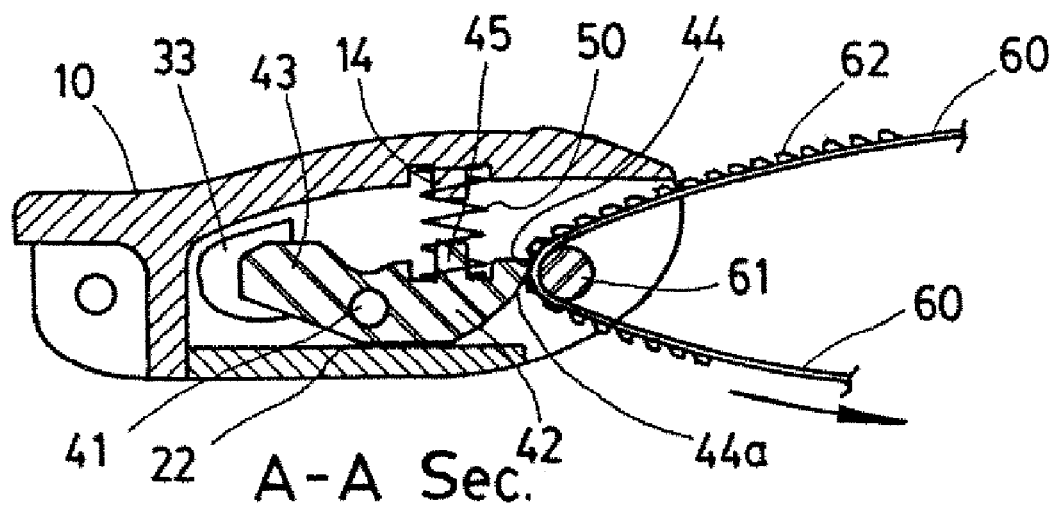
FIG. 3 is a sectional view taken along line A-A of FIG. 1 where the engagement tooth and the rack teeth are engaged in a fastened position.

Referring to FIG. 3, the strap 60 has a plurality of parallel rack teeth 62 on a portion of an upper surface, Referring to FIGS. 3 to 6, an operation of the invention will be described in detail below. In an inoperative position (see FIGS. 3 and 5), the arms 30 are not pressed with the inclined bottom planes 33a of the protrusions 33 being disengaged from the rounded top corners 43a of the rear section 43, the front section 42 being biased downward by the expanding spring 50, and the engagement tooth 44 being lockingly engaged with one of the rack teeth 62 (i.e., the strap 60 being prevented from moving in a direction as indicated by arrow in FIG. 3). Hence, the strap 60 is fastened.

Figure 4:
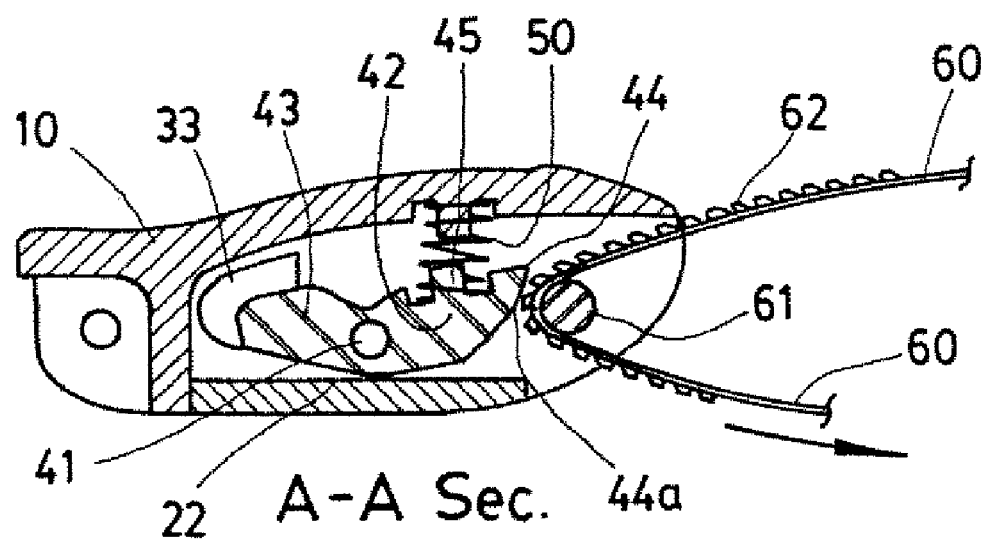
FIG. 4 is a view similar to FIG. 3 where the engagement tooth and the rack teeth are not engaged so as to adjust the strap tension.
Figure 6:
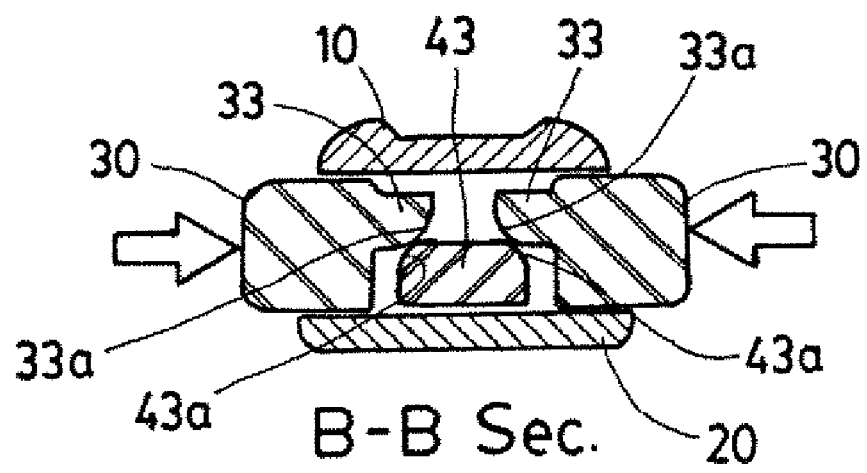
FIG. 6 is a view similar to FIG. 5 where both arms are pressed toward each other to elastically lower the rear section of the ratchet so as to disengage the engagement tooth from the rack teeth prior to tension adjustment.

As shown in FIGS. 4 and 6, an individual may press the arms 30 toward each other to lower the inclined bottom planes 33a of the protrusions 33. Hence, the rounded top corners 43a of the rear section 43 are pressed down by the inclined bottom planes 33a of the protrusions 33. And in turn, the front section 42 pivots upward about the pins 41. Also, the ratchet 44 moves upward. Hence, a gap between the ratchet 44 and the strut 61 increases to permit the strap 60 including its rack teeth 62 to freely pass (i.e., the strap 60 being unfastened for being ready to adjust its tension by pulling in a direction as indicated by the arrow shown in FIG. 4). At the same time, the spring 50 is compressed to store elastic energy.

Figure 5:
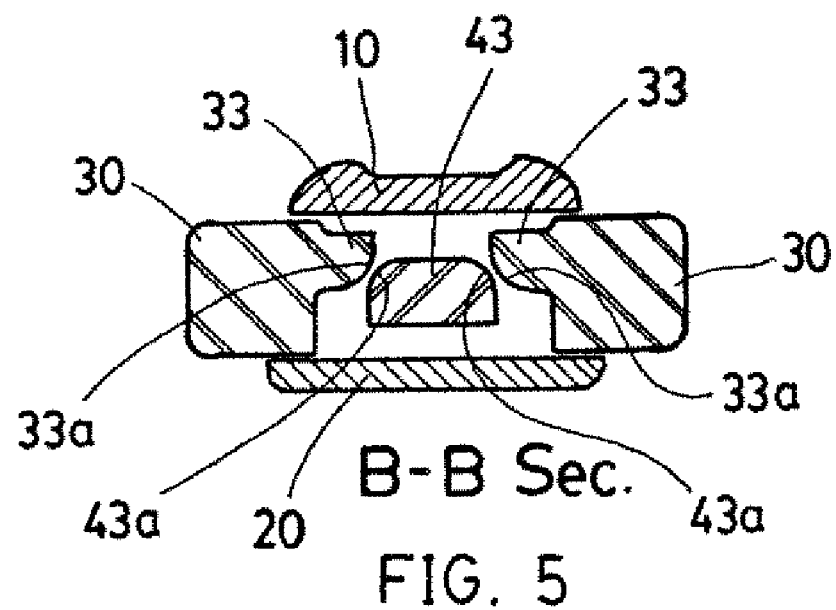
FIG. 5 is a sectional view taken along line B-B of FIG. 1 where both arms are not activated in the fastened position.

The spring 50 will immediately release its stored energy to push the front section 42 downward after releasing the arms 30 after adjusting strap tension. As a result, the buckle returns to its inoperative position as shown in FIGS. 3 and 5. At this position, the strap 60 is lockingly engaged with the ratchet 40. In other words, it is possible of adjusting the buckle in discrete increments to tighten the strap 60.

As shown in FIGS. 3 and 4, the rack teeth 62 are of triangular in cross-section (i.e., any tooth having an inclined plane and a flat shoulder abutting an immediately adjacent tooth) and the engagement tooth 44 is shaped to complement any one of the rack teeth 62. A pulling of the strap 60 is thus made possible with the engagement tooth 44 being disengaged from one of the rack teeth 62 after pressing the arms 30 (see FIG. 4). Hence, an adjustment of the tension of the strap 60 can be made in discrete increments in order to tighten the strap 50. To the contrary, the engagement tooth 44 engages with one of the rack teeth 62 due to the lowering of the front section 42 after releasing the arms 30 after adjusting strap tension. As an end, the strap 60 is locked in this position.

In brief, pressing the arms 30 will unfasten the strap 60 for adjusting strap tension. Releasing the arms 30 will fasten the strap 60 in its tightened, locked position. Moreover, the lever-like ratchet 40 makes the strap tension adjustment operation more precise and reliable.

While the invention herein disclosed has been described by means of specific embodiments, numerous modifications and variations could be made thereto by those skilled in the art without departing from the scope and spirit of the invention set forth in the claims.

What is claimed is:

1. A buckle comprising;
    two arms having a rear protrusion on an inner surface, the protrusion having a shaped bottom plane, and a front protuberance on the inner surface, the protuberance having a longitudinal hole;
    a cover;
    a base including two opposite holed ears and two opposite pins with the longitudinal holes of the protuberances pivotably put thereon such that the arms are adapted to pivot about the pins, the base being assembled with the cover to form a housing having its rear end secured to an object, the housing comprising a front opening, and two side openings with the arms being disposed therein,
    a strut disposed across the front opening;
    a strap looping around the strut and having a plurality of rack teeth on an upper surface;
    a lever member pivotably disposed on the holed ears, the lever member comprising a front section having a detent member, and a rear section; and
    a biasing member anchored between the front section and the cover;
    wherein in an inoperative position the bottom planes of the protrusions are disengaged from the rear section and the detent member being lockingly engaged with one of the rack teeth by the expanding biasing member; and
    wherein the arms are adapted to press toward each other to lower the bottom planes of the protrusions to push down the rear section and lift the front section with the biasing member being compressed by pivoting about the holed ears, thereby disengaging the detent member from the rack teeth to allow the strap to freely pass through a gap between the detent member and the strut.

2. The buckle of claim 1, wherein the detent member is a ratchet tooth.

3. The buckle of claim 1, wherein the detent member has an inclined plane or a curved plane.

4. The buckle of claim 1, wherein the rear section has two top corners being rounded or inclined.

* * * * *